(12) United States Patent
Casavant et al.

(10) Patent No.: US 11,707,630 B2
(45) Date of Patent: Jul. 25, 2023

(54) HIS-BUNDLE OR BUNDLE BRANCH PACING CAPTURE VERIFICATION

(71) Applicant: Cardiac Pacemakers, Inc., St. Paul, MN (US)

(72) Inventors: David Arthur Casavant, Reading, MA (US); Deepa Mahajan, North Oaks, MN (US); David L. Perschbacher, Coon Rapids, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 742 days.

(21) Appl. No.: 16/659,261

(22) Filed: Oct. 21, 2019

(65) Prior Publication Data

US 2020/0129772 A1 Apr. 30, 2020

Related U.S. Application Data

(60) Provisional application No. 62/750,052, filed on Oct. 24, 2018.

(51) Int. Cl.
*A61N 1/37* (2006.01)
*A61N 1/365* (2006.01)

(52) U.S. Cl.
CPC ....... *A61N 1/3712* (2013.01); *A61N 1/36507* (2013.01); *A61N 1/36521* (2013.01); *A61N 1/36564* (2013.01); *A61N 1/36578* (2013.01); *A61N 1/36585* (2013.01)

(58) Field of Classification Search
CPC .... A61N 1/3712; A61N 1/371; A61N 1/3684; A61N 1/36507; A61N 1/36521; A61N 1/36564; A61N 1/36578; A61N 1/36585
See application file for complete search history.

(56) References Cited

U.S. PATENT DOCUMENTS 8,588,907 B2 11/2013 Arcot-Krishnamurthy et al.
2019/0134404 A1\* 5/2019 Sheldon ................. A61B 5/686

\* cited by examiner

*Primary Examiner* — Lindsey G Wehrheim
(74) *Attorney, Agent, or Firm* — Schwegman Lundberg & Woessner, P.A.

(57) ABSTRACT

Systems and methods for pacing cardiac conductive tissue are described. In an embodiment, a medical system includes an electrostimulation circuit to generate pacing pulses to stimulate a His bundle or a bunch branch. A sensing circuit senses a far-field ventricular activation, determines a cardiac synchrony indicator using the far-field ventricular activation in response to His bundle or bundle branch pacing, and verifies His-bundle capture status using the determined cardiac synchrony indicator. The system can determine a pacing threshold using the capture status under different stimulation strength values. The electrostimulation circuit can deliver stimulation pulses in accordance with the determined pacing threshold.

20 Claims, 5 Drawing Sheets

HIS-BUNDLE OR BUNDLE BRANCH PACING CAPTURE VERIFICATION

CLAIM OF PRIORITY

This application claims the benefit of priority under 35 U.S.C. § 119(e) of U.S. Provisional Patent Application Ser. No. 62/750,052, filed on Oct. 24, 2018, which is herein incorporated by reference in its entirety.

TECHNICAL FIELD

This document relates generally to medical systems, and more particularly, to systems, devices and methods for pacing of cardiac conductive tissue, such as a His bundle or a bundle branch.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through specialized electrical conduction pathways in the RA to a midway point known as the AV node. Thereafter, the action potentials propagate through the His bundle, left and right bundle branches and ultimately to the terminal Purkinje fibers that distribute electrical activation to various regions of the heart and ultimately excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction near the junction of the His bundle and the bifurcation of the left and right bundles may cause dyssynchronous contraction of the ventricles of the heart, resulting in poor hemodynamic performance, including a diminished blood supply to the heart and the rest of the body. For example, a block in the transmission of the action potentials within the left bundle fascicle of the His bundle can cause irregular or dyssynchronous contractions of the ventricles, resulting in an abnormal contraction of the heart.

Artificial cardiac pacing system have been used to rectify cardiac dyssynchrony and to improve hemodynamic performance. The artificial cardiac pacing system can provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apex pacing directly excites the ventricular myocardium, rather than propagating the action potentials through the natural conduction pathways. Studies have shown that, in some patients, long-term RV apex pacing may result in loss of synchronous mechanical contraction of RV and LV, partially due to the interventricular delay in impulse propagation to the left ventricle. Consequently, permanent changes in myocardial perfusion and structure may develop over time in these patients, which may further decrease cardiac output and deteriorate ventricular function. BiV pacing involves RV pacing via one lead, and LV pacing via another lead, and has been demonstrated to restore synchronized contraction of both ventricles. However, the potential adverse impact on ventricular function produced by the RV apex pacing may still exist in BiV pacing. Additionally, compared to cardiac depolarization through AV node activation and propagation through the natural conduction pathways, the BiV pacing may not produce similarly coordinated cardiac contractions. Moreover, the surgical procedure for placing the LV lead through the coronary sinus and into a vein on the left ventricular wall can be complex and challenging in some patients.

OVERVIEW

Disclosed herein are systems, devices, and methods for pacing cardiac conductive tissue. An embodiment of the system may include an electrostimulator to generate electrostimulation pulses to stimulate a His bundle or a bundle branch. The system may sense a far-field ventricular activation (FFVA), determine a cardiac synchrony indicator using the FFVA sensed during the stimulation of the His bundle or the bundle branch, and verify His-bundle capture status using the determined cardiac synchrony indicator. In some examples, the system may determine a HBP threshold, and the electrostimulator may deliver HBP pulses in accordance with the determined HBP threshold.

Example 1 is a system for pacing a heart. The system comprises an electrostimulation circuit configured to generate electrostimulation pulses to stimulate a His bundle or a bundle branch of the heart, a sensing circuit configured to sense a far-field ventricular activation, and a control circuit that includes a capture verification circuit. The capture verification circuit is configured to determine a cardiac synchrony indicator using the sensed far-field ventricular activation in response to the electrostimulation of the His bundle or the bundle branch, and verify a capture status using the determined cardiac synchrony indicator.

In Example 2, the subject matter of Example 1 optionally includes the sensing circuit that can be configured to sense the far-field ventricular activation including a far-field electrogram in response to the stimulation of the His bundle or the bundle branch, and to measure a QRS width using the sensed far-field electrogram. The capture verification circuit can be configured to verify the capture status using the measured QRS width.

In Example 3, the subject matter of Example 2 optionally includes the capture verification circuit that can be configured to verify the capture status as one of a His-bundle capture if the measured QRS width falls below a threshold, or a para-Hisian capture or a loss of capture if the measured QRS width exceeds the threshold.

In Example 4, the subject matter of any one or more of Examples 1-3 optionally includes the sensing circuit that can be configured to sense the far-field ventricular activation including a far-field electrogram in response to the stimulation of the His bundle or the bundle branch, and the capture verification circuit that can be configured to verify the capture status using a comparison of the sensed far-filed electrogram to a morphology template.

In Example 5, the subject matter of any one or more of Examples 1-4 optionally includes the sensing circuit that can be configured to sense the far-field ventricular activation using a ventricular electrode and a reference electrode.

In Example 6, the subject matter of any one or more of Examples 1-4 optionally includes the sensing circuit that can be configured to sense the far-field ventricular activation using an atrial electrode and a reference electrode.

In Example 7, the subject matter of any one or more of Examples 1-4 optionally includes the sensing circuit that can be configured to sense the far-field ventricular activation using a His-bundle electrode and a reference electrode.

In Example 8, the subject matter of any one or more of Examples 1-4 optionally includes the sensing circuit that can be configured to sense the far-field ventricular activation using chest electrodes.

In Example 9, the subject matter of any one or more of Examples 1-8 optionally includes the capture verification circuit that can be configured to determine the cardiac synchrony indicator further using heart sounds information or endocardial acceleration information in response to the stimulation of the His bundle or the bundle branch.

In Example 10, the subject matter of any one or more of Examples 1-9 optionally includes the capture verification circuit that can be configured to determine the cardiac synchrony indicator further using cardiac impedance information in response to the stimulation of the His bundle or the bundle branch.

In Example 11, the subject matter of any one or more of Examples 1-10 optionally include the capture verification circuit that can be configured to determine the cardiac synchrony indicator further using cardiac pressure information in response to the stimulation of the His bundle or the bundle branch.

In Example 12, the subject matter of any one or more of Examples 1-11 optionally includes the control circuit that can be configured to adjust a therapy parameter using the verified capture status, and to control the stimulation of the His bundle or the bundle branch according to the adjusted therapy parameter.

In Example 13, the subject matter of Example 12 optionally includes the therapy parameter that can include one or more of: a pacing site for delivering stimulation pulses; a pulse amplitude; a pulse width; or a pulse rate.

In Example 14, the subject matter of any one or more of Examples 12-13 optionally includes the control circuit that can be configured to, in response to a para-Hisian capture or a loss of capture produced by stimulation at a first His bundle site, control the electrostimulation circuit to stimulate a second His bundle site more distal than the first His bundle site or a left bundle-branch site.

In Example 15, the subject matter of any one or more of Examples 1-14 optionally includes the control circuit that can include a pacing threshold test circuit coupled to the capture verification circuit. The capture verification circuit can be configured to verify capture status in response to electrostimulation pulses having multiple stimulation strength values according to a threshold test protocol. The pacing threshold test circuit can be configured to determine, using the verified capture status, a pacing threshold.

Example 16 is a method, comprising steps of: generating electrostimulation pulses to stimulate a His bundle or a bundle branch of the heart; sensing a far-field ventricular activation in response to the stimulation of the His bundle or a bundle branch; and determining a cardiac synchrony indicator using the sensed far-field ventricular activation; and verifying a capture status using the determined cardiac synchrony indicator.

In Example 17, the subject matter of Example 16 optionally includes the far-field ventricular activation that can include a far-field electrogram, and wherein verifying the capture status can include using a QRS width from the far-field electrogram.

In Example 18, the subject matter of Example 16 optionally includes the far-field ventricular activation that can include a far-field electrogram, and wherein verifying the capture status can include using a comparison of the sensed far-filed electrogram to a morphology template.

In Example 19, the subject matter of any one or more of Examples 16-18 optionally includes: in response to the stimulation of the His bundle or the bundle branch, receiving one or more physiologic information including heart sounds information, endocardial acceleration information, cardiac impedance information, cardiac pressure information; and determining the cardiac synchrony indicator further using the received one or more physiologic information.

In Example 20, the subject matter of any one or more of Examples 16-19 optionally includes adjusting a therapy parameter using the verified capture status, and delivering stimulation pulses to the His bundle or the bundle branch according to the adjusted therapy parameter.

In Example 21, the subject matter of Example 20 optionally includes, in response to a para-Hisian capture or a loss of capture produced by stimulation at a first His bundle site, delivering stimulation pulses to a second His bundle site more distal than the first His bundle site or a left bundle-branch site.

In Example 22, the subject matter of any one or more of Examples 16-21 optionally includes verifying capture status in response to electrostimulation pulses having multiple stimulation strength values according to a threshold test protocol, and determining a pacing threshold using the verified capture status.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Figure 1:
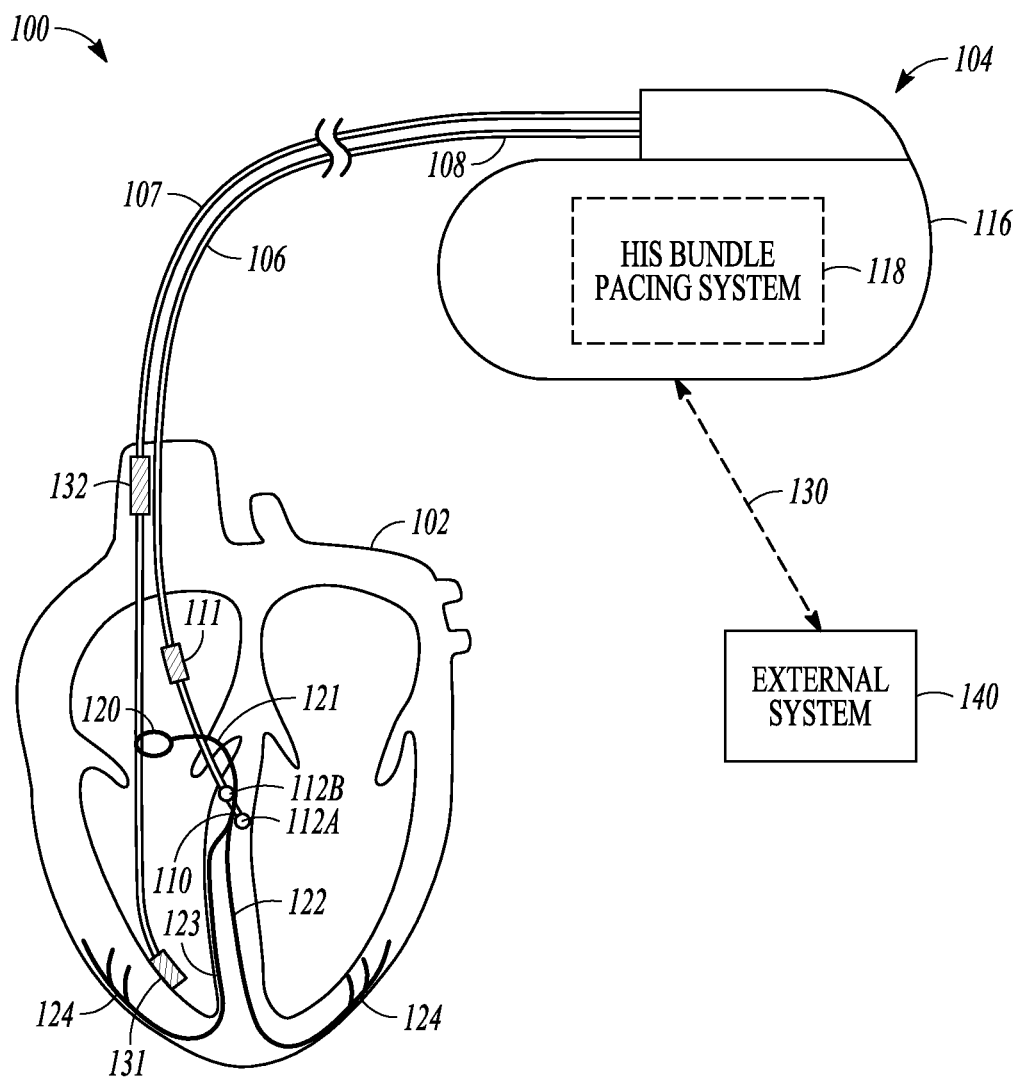
FIG. 1 illustrates generally an example of a cardiac disease management system and portions of an environment in which the system may operate.

Hemodynamic response to artificial pacing can depend on many factors, including pacing site selection and pacing configurations. Many patients receiving artificial pacing therapy have an intact His bundle and the natural cardiac electrical conduction system in the ventricles, and therefore having normal ventricular activation. Conventional cardiac pacing such as long-term RV apex pacing may cause a decrease in cardiac efficiency due to the uncoordinated contraction sequence, and eventually exhibit adverse long-term effects. Dyssynchronous contraction of the ventricles occurs during conventional right ventricular pacing because the activation sequence can be much slower and propagate slowly from the right to the left ventricle across the interventricular septum, thereby causing ventricular dyssynchrony. This sequence of activation results in an uncoordinated contraction which does not occur during biventricular activation through the natural conduction system of the heart. The cells of the natural conduction system can propagate an activation signal about four times faster than working myocardium. A cardiac rhythm or functional management device configured to pace the His bundle is an alternative to conventional ventricular pacing in some patients. His-bundle pacing (HBP) may activate the heart's natural His-Purkinje system in some patients, and produce efficient and coordinated cardiac contractions. The potentially long-term harmful hemodynamic effects that may occur from continuous RV apex pacing may also be eliminated or reduced.

However, when not being successful, the HBP may not adequately restore cardiac synchrony. In some instances, the electrical stimulation may lose its ability to activate (or capture) the His bundle, but only activates the para-Hisian myocardium surrounding the His bundle. Stimulating muscles near the His bundle may cause dyssynchronous patterns similar to RV apical pacing. This undesirable effect is referred to as para-Hisian capture. Simultaneous capture of the His bundle and para-Hisian muscle (also known as a non-selective His-bundle capture) can be as clinically effective as the His-bundle only capture absent of para-Hisian muscle capture (also known as a selective His-bundle capture). This is because the ventricles are activated predominately by the rapidly conducting natural conduction system. Another undesirable effect of HBP is known as a complete loss of capture (LOC), where the HBP pulses capture neither the para-Hisian myocardium nor the His bundle. Therefore, verification of His-bundle capture status can be an important function of a HBP device in monitoring and assessing HBP therapy efficacy.

The ability of HBP to restore cardiac synchrony may also be dependent on the pacing site relative to the blockage site along the His-Purkinje system, such as at the His bundle. Ventricular dyssynchrony in many heart failure (HF) patients may be attributed to various degrees of left bundle branch block (LBBB), which causes delayed LV depolarization lagging behind RV depolarization. In some patients, right bundle branch block (RBBB) may also result in dyssynchrony. Effective propagation of the action potentials through the His-Purkinje system to restore cardiac synchrony can be achieved only if the HBP pulses are delivered distal to the blockage site. If the HBP pulses are delivered proximal to the blockage site, even if the proximal portion of the His bundle is activated, the action potential cannot bypass the blockage and propagate to the ventricles through the His-Purkinje system. Consequently, no cardiac synchrony may be restored.

Conventionally, capture status verification techniques have relied upon evoked response detection that is muscular in origin. Measuring the evoked His bundle depolarization during HBP represents a technical challenge. For example, the evoked His-bundle depolarization may have a relatively small amplitude and very short in duration, and is overwhelmed by post-pacing polarization effect introduced by the HBP pulses. Additionally, because some patients receiving HBP therapy often have various degrees of heart block, and the electrodes for sensing the evoked His-bundle response may be positioned in close proximity to atrial myocardium, the sensed evoked His-bundle response may be confounded by atrial activation. As such, programming the His-bundle sense channel to a high sensitivity in order to sense an evoked response may introduce the risk of over-sensing of atrial activity. In some cases, the over-sensing of atrial activity may inappropriately inhibit the HBP therapy, and lead to critical consequences particularly in patients with heart block, and who are pacemaker-dependent.

The capture status verification may also help determine an individualized HBP threshold. The HBP threshold represents minimal energy required to excite the His bundle (or a bundle branch) and to correct the cardiac conduction abnormality. Typically, to ensure effective capture, pacing output may be set to the pacing threshold plus a safety margin. The HBP threshold may vary according to an individual's His bundle anatomy and with lead type and positioning, and may vary over time in a patient due to changes in patient pathophysiology (e.g., development of a new medical condition such as myocardial ischemia, fibrotic scarring, or progression of an existing medical condition), medication, or lead migration, dislodgment, or micro-dislodgment, among other causes. Determining pacing threshold and tracking changes of the pacing threshold over time in a patient can be beneficial to ensure continued therapy, or to titrate individualized electrostimulation therapy to achieve desired patient outcome.

For at least the above reasons, the present inventors have recognized that there is an unmet need for an artificial pacing system that can more effectively detect His-bundle capture status, automatically determine or adjust individualized HBP threshold, and adjust therapy in response to HBP delivered in accordance with the individualized HBP threshold. Embodiments of the present subject matter provide systems, devices, and methods to improve HBP therapy efficacy. An exemplary medical system includes circuitry for generating HBP pulses to stimulate a His bundle, or a bundle branch of the heart such as left bundle branch, and detecting a far-field ventricular activation (FFVA). A control circuit may determine a cardiac synchrony indicator using the sensed FFVA in response to the stimulation of the His bundle or the bundle branch, and verify His-bundle capture status using the determined cardiac synchrony indicator. In various examples, the control circuit may determine cardiac synchrony using a QRS width measured from a far-filed electrogram. A narrow QRS may be indicative of His-bundle capture and restored synchronous ventricular contractions. Conversely, a wide QRS may be indicative of dyssynchronous ventricular contractions, unsuccessful His-bundle capture, or HBP pacing site proximal to or above the blockage site. The control circuit may additionally determine a pacing threshold for stimulating the His bundle or a bundle branch. The electrostimulation circuit may deliver HBP pulses in accordance with the determined HBP threshold.

The systems, devices, and methods discussed in this document may improve the technology of cardiac pacing in patients with cardiac disease, such as heart failure. HBP may activate natural His-Purkinje system, thereby preserving ventricular synchrony and improving cardiac performance without structural and functional impairment to the heart. A technological challenge in HBP is to verify His-bundle capture status, and determine appropriate, individualized HBP threshold to ensure reliable activation of the His-Purkinje system. While a high stimulation output may more likely to produce His-bundle capture, it may result in unintentional capture of the right atrium and consume more battery power. The present subject matter can improve automated His-bundle capture verification and individualized HBP threshold test, with little to no additional cost or system complexity. The His-bundle pacing as discussed in the present document can leverage the electrophysiology of the His bundle region, and improve pacing efficiency utilizing the natural conduction mechanisms of the heart, while reducing long-term harmful hemodynamic effects associated with RV apex pacing. An embodiment of the His-bundle capture verification discussed herein is using QRS width or morphology of FFVA. With improved synchrony and cardiac performance, fewer unnecessary medical interventions, such as drugs, procedures, or device therapies, may be scheduled, prescribed, or provided to such patients. As a result, overall system cost savings may be realized.

The His-bundle capture verification using FFVA and individualized pacing threshold testing as discussed in this document may also improve the functionality of a cardiac pacing system or device. Device memory usage may be more efficient by storing HBP thresholds that are clinically more relevant to titrating cardiac pacing therapy to improve therapy efficacy. Automatic HB capture verification and threshold monitoring algorithms may also facilitate remote patient monitoring. The HBP threshold as determined using the capture verification using the FFVA may not only improve effectiveness of HBP therapy, but may extend battery life and implantable device longevity as well with reduced pacing energy and avoidance of unnecessary device therapies. Additionally, device size may be reduced to achieve existing performance metrics.

While His-bundle pacing is specifically discussed in this document, this is meant only by way of example and not limitation. It is within the contemplation of the inventors, and within the scope of this document, that the systems, devices, and methods discussed herein may be applied to stimulate right or left bundle branches or fascicles, the Purkinje fibers, among other conductive cardiac tissue.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG.1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG.1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-112B, are positioned in or on a His bundle 121, a region distal to the blocked or slowly conducting AV node and in the AV septum, an interventricular septum region, or a right atrial region near the His-bundle 121. Alternatively, one or more of the electrodes 112A-112B, or other electrodes on the lead 106, may be configured to stimulate a bundle branch, such as a left bundle branch or a right bundle branch. As part of the specialized electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-112B, are positioned at or near other parts of the natural conduction pathways, such as one of the bundle branches 122 or 123, the Purkinje fibers 124, or other conductive tissue, in addition to or in lieu of a region at or near the His bundle 121.

In an example, the lead 106 may be a single pass lead having a plurality electrodes for stimulating multiple cardiac sites, including electrodes disposed at or near the His bundle (e.g., the electrodes 112A-112B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. As to be discussed in the following, the cardiac disease management system 100 may deliver pacing pulses at the His bundle or a bundle branch site, and sense a FFVA to verify whether the pacing pulses capture the His-bundle or the bundle branch. In some examples, the cardiac disease management system 100 may include one or more leadless stimulators/sensors untethered to a lead and in wireless communication with the IMD 104. The leadless stimulators/sensors may deliver electrostimulation, sense a physiological signal, such as cardiac electrical signals in response to cardiac stimulation, and transmit the sensed data to the IMD 104.

The IMD 104 may include a hermetically sealed housing 116 that houses one or more of an electrostimulation circuit, a sensing circuit, a control circuit, a communication circuit, and a battery, among other components. In an example, the IMD 104 includes a His-bundle pacing system 118 configured to generate His-bundle pacing (HBP) pulses to stimulate the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-112B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or multipolar (e.g., bipolar or quadripolar) His-bundle pacing may be selected by a system user from a plurality of candidate electrodes from a given lead or multiple separate leads comprising the pacing system, and programmed into the His-bundle pacing system 118. In some examples, HBP pulses may be provide by a leadless device, such as a leadless cardiac pacemakers (LCP). One or more electrodes may be distributed on the body of the LCP and in contact with His-bundle region to deliver the HBP pulses.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others.

In various examples, the His-bundle pacing system 118 may sense far-field ventricular activation (FFVA) using one or more electrodes or a physiologic sensor. The FFVA can be a signal recorded from afar at a given moment in time by two electrodes having similar source impedance. The FFVA may be sensed in response to electrostimulation to the His bundle or a bundle branch. In an example, the FFVA includes an EGM sensed via an electrode positioned within, or on the epicardial surface of, a ventricle. In an example as illustrated in the FIG. 1, the lead system may include a ventricular lead 107 including at least one RV electrode 131, which may be a tip electrode, a ring electrode, or a coil electrode. The His-bundle pacing system 118 may sense a FFVA signal (e.g., a far-field EGM) using the RV electrode 131 (e.g., as a cathode) and a reference electrode (e.g., as an anode). The EGM sensed as such using an RV electrode represents far-field LV activation, or far-field BiV activation. In an example, the reference electrode is a proximal electrode 132 on the ventricular lead 107. The proximal electrode 132 may be a coil electrode situated at the superior vena cava (SVC) of the heart. The distal electrode 131 and the proximal electrode 132 may also be used to deliver defibrillation shocks to correct ventricular tachyarrhythmia. In an example, the reference electrode may include the housing 116 or an electrode therein. In another example, the FFVA signal may be sensed using an atrial electrode 111 associated with the lead 106 and positioned in the RA and a reference electrode. In yet another example, the FFVA signal may be sensed using a His-bundle electrode associated with the lead 106 (e.g., electrode 112A or 112B) and a reference electrode. Examples of the reference electrode may include the housing 116 or an electrode therein. In another example, the FFVA signal may include a subcutaneous ECG signal sensed using subcutaneous chest electrodes such as located at the housing 116. In yet another example, the FFVA signal may include surface ECG signal sensed using skin electrodes attached to the body surface.

The His-bundle pacing system 118 may determine a cardiac synchrony indicator using the sensed FFVA in response to the stimulation of the His bundle or a bundle branch. In many HF patients, ventricular dyssynchrony may be attributed to various degrees of left bundle branch block (LBBB), which causes LV depolarization lagging behind RV depolarization. Ventricular activation (e.g., an EGM) sensed by an electrode situated in a ventricular (e.g., RV), His bundle, or an atrium, may have a signal pattern characterized by substantial LV-RV activation delay and wide QRS complex. When HBP pulses are delivered at a His-bundle site distal to the blockage site or at a bundle branch site and successfully capture the His bundle or the bundle branch, the action potential may propagate along the His-Purkinje system, and produce synchronized contractions in both LV and RV. The cardiac synchrony can be manifested in a FFVA as a narrow QRS complex. Conversely, if HBP pulses are delivered at a site proximal to the blockage site (i.e., above the blockage site), or fail to capture the His bundle or the bundle branch (e.g., LOC, or para-Hisian myocardium capture), no restoration of cardiac dyssynchrony can be achieved; and a wide QRS can be detected from the FFVA. Therefore, His-bundle capture status may be determined by monitoring the FFVA. In some examples, the FFVA signal can be filtered using a bandpass filter with a wide passband, such as approximately 3-50 Hz, and the QRS complex can be detected using the filtered FFVA signal. Such a wide band filter may help improve the accuracy of QRS width measurement.

In accordance with the His-bundle capture status, the His-bundle pacing system 118 may adjust one or more pacing parameters, such as increasing the pacing amplitude to improve His-bundle capture. The His-bundle pacing system 118 may additionally determine a HBP threshold representing a threshold stimulation strength capable of capturing the His bundle. The His-bundle pacing system 118 may deliver HBP pulses according to the determined HBP threshold. Examples of His-bundle capture verification using FFVA are discussed below, such as with reference to FIGS. 2 and 3.

The IMD 104 may communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry using, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display received information to the user, and receive user input for operation control of the IMD 104. In an example, the external system 140 may be configured to verify pacing capture status, perform pacing threshold test to determine a HBP threshold. The capture verification and threshold testing may be executed periodically, or triggered by a specific event such as a user command. A user may use the external system 140 to program the IMD 104, such as to configure a pacing vector (e.g., specifying anode and cathode electrodes) to deliver HBP, or to configure a sense vector to sense a physiological signal.

The external system 140 may include a remote device in a location relatively distant from the IMD 104 and in communication with the proximal external device via a telecommunication network. The remote device can evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104.

By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, capture verification, or classification of capture types, among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
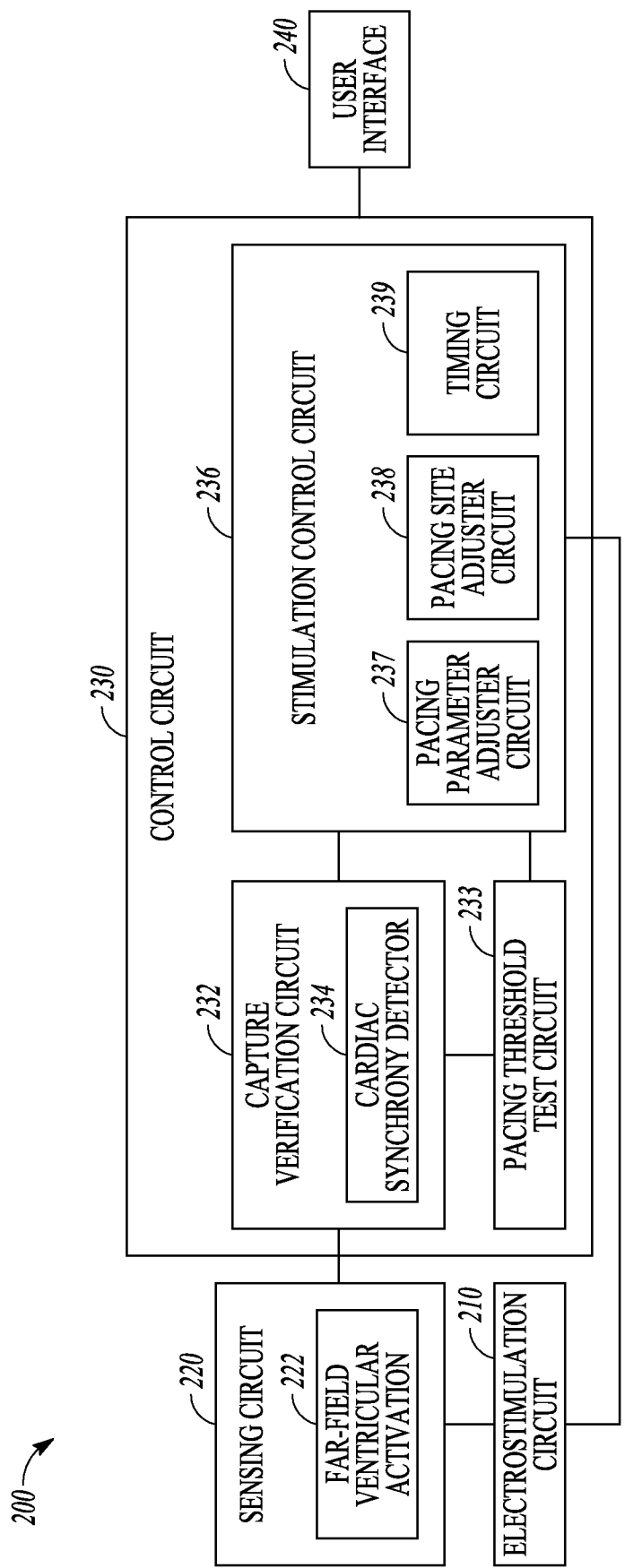
FIG. 2 is a block diagram illustrating an example of portions of a His-bundle pacing system.

FIG. 2 is a block diagram illustrating an embodiment of portions of a His-bundle pacing system 200. The His-bundle pacing system 200 represents an embodiment of the His-bundle pacing system 118, and may include an electrostimulation circuit 210, a sensing circuit 220, a control circuit 230, and a user interface 240.

The electrostimulation circuit 210 may be configured to generate stimulation energy for delivery to the heart 102, such as via one or more leads and the associated electrodes. The electrostimulation circuit 210 may be configured to generate His-bundle pacing (HBP) pulses for delivery to a target pacing site at or near the His bundle such as via the lead 106 and one or more of the electrodes 112A-112B. The target site may include an interventricular septum region or a right atrial region near the His-bundle, or other conductive tissue such as right or left bundle branches or fascicles, or Purkinje fibers. In an example, the HBP pulses may be delivered in multiple cardiac cycles, such that at least one pulse is delivered within each of the multiple cardiac cycles. In various examples, the electrostimulation circuit 210 may additionally generate electrostimulation to stimulate non-cardiac tissue, such as nerve tissue, muscle tissue, or other excitable tissue.

The electrostimulation circuit 210 may generate HBP pulses according to one or more stimulation parameters, such as provided by control circuit 230. Examples of the stimulation parameters may include information about stimulation site, stimulation strength, stimulation mode, or stimulation timing, among other parameters. Stimulation site includes information about pacing site, pacing vector configuration (e.g., anode and cathode electrodes), unipolar or bipolar pacing, cardiac resynchronization therapy (CRT), BiV pacing, or synchronized left ventricle (LV)-only pacing, single site pacing of only one site of a heart chamber (e.g., the left ventricle), or multisite pacing (MSP) of two or more sites of a heart chamber within the same cardiac cycle, among others. Stimulation strength parameters determine the amount of energy delivered to the pacing site, and may include pulse amplitude, pulse width, pulse frequency, pulse waveform, duty cycle, or stimulation duration.

Stimulation mode includes, by way of example and not limitation, a His-bundle only mode, an atrial-Hisian (AH) pacing mode, a His-ventricular (HV) pacing mode, or an atrial-His-ventricular (AHV) pacing mode. In the His-bundle only pacing mode, atrial activation may be sensed by the His-bundle pacing electrode, such as by using a single pass lead, or a leadless pacemaker having a form factor with multiple electrodes positioned such that reliable atrial sensing may be achieved. In the AH pacing mode, the HBP pulses may be delivered only when intrinsic atrial activation (As), or atrial pacing (Ap), fails to produce propagatable depolarization of the AV node and the His bundle. The AH pacing mode may be suitable for patients with varying degrees of heart block or sick sinus syndrome. The HV pacing mode involves sequential pacing of the His bundle and the ventricle. The ventricular pacing may be provided in a demand mode, such that the ventricular pacing pulses are delivered only when the His pacing fails to produce propagatable depolarization of the ventricles. The HV pacing mode may be indicated for patients with persistent or chronic atrial fibrillation, or who have been treated with atrioventricular node ablation or drugs to slow and the rapid ventricular rhythm that often results and allow HBP to predominate. The AHV pacing mode involves sequential atrial, Hisian, and ventricular pacing. One or more of the His-bundle pacing or the ventricular pacing may be delivered in a demand mode. The AHV pacing mode may be indicated for patients with cardiac dyssynchrony and having received cardiac resynchronization therapy, patients suffering from HF with LBBB, HF induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an AS or an AP event. An AH timing represents a latency period, within a cardiac cycle, from an intrinsic AS event or an AP event to the delivery of a HBP pulse. In demand HV pacing mode, the ventricular pacing pulses are timed relative to a His pacing event. The HV timing represents a latency period, within a cardiac cycle, from a His bundle event (e.g., a HBP pulse) to the delivery of ventricular pacing pulse. In an example, if a HBP pulse fails to induce ventricular depolarization, a backup ventricular pacing may be delivered at the end of the HV timing. The stimulation timing parameters may additionally include parameters associated with CRT or MSP therapy, such as atrial-ventricular delay (AVD) representing a latency period from an AS or AP event to ventricular pacing, an RV-LV interventricular pacing delay (VVD) representing a time delay between ventricular pacing at the left and right ventricles, or intra-ventricular pacing delay representing a time delay between pacing at multiple site of a ventricle.

The electrostimulation circuit 210 may be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP, selective HBP causes only the excitation (depolarization) of the His bundle, without direct excitation of para-Hisian myocardium adjacent to the His bundle. Non-selective HBP directly causes excitation of both the His bundle and the para-Hisian myocardium. If the HBP pulses cause only excitation of the para-Hisian myocardium or other un-intended cardiac tissue, without direct excitation of the His-bundle fibers, then a para-Hisian pacing results. If no tissue excitation is induced by HBP (e.g., neither the para-Hisian myocardium capture nor the His-bundle capture), then a complete loss of capture (LOC) results.

The electrostimulation circuit 210 may be capable of generating backup pacing pulses for delivery to the heart to excite the myocardium and prevent asystole. The backup pacing pulses may be delivered when a loss of capture is produced, or alternatively when para-Hisian capture is produced. The backup pacing may be delivered to a target ventricular site via a lead with associated electrodes disposed in or on a ventricle, such as a right ventricle. Additionally or alternatively, the backup pacing may be delivered to the His bundle, such as the site for delivering HBP pulses, via the same His-bundle pacing lead with associated electrodes. In an example, the backup pacing may include high-output pacing (HOP) pulses with higher pacing energy than conventional pacing pulses. The HOP pulse may be a biphasic or multiphasic waveform. In an example, the HOP pulse may have a peak-to-peak voltage amplitude of 5-8 volts, and a pulse duration of 50-70 msec. With higher amount of energy delivered to the myocardium, the HOP pulse may increase myocardial contractility and improve systolic function. However, chronic HOP pacing may over-stress the heart and potentially be hazardous in some heart failure patients.

According, in some examples, the HOP pulses may be delivered on an intermittent basis, such that the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al. U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

The sensing circuit 220 may be coupled to one or more electrodes or physiologic sensors to sense a physiologic signal indicative of a response of a portion of the heart 102 to the delivery of HBP pulses. Examples of the sensed signals may include an electrocardiogram (ECG), an electrogram (EGM) of a portion of the heart such as atrial EGM, ventricular EGM, or evoked His potential, an impedance signal, a heart sound signal, or a pressure signal, among other physiological or hemodynamic signals indicative of a tissue response to the delivery of HBP pulses.

In various examples, the sensing circuit 220 may sense a far-field ventricular activation (FFVA) signal 222. The FFVA signal 222 may include a far-field electrical signal (e.g., an electrogram) indicative of electrical synchrony of depolarizations of the left and right ventricles in response to the HBP delivery. The far-field EGM may be sensed using a unipolar or a bipolar configuration. In an example, the far-field EGM may be sensed via a ventricular electrode positioned within or on the epicardial surface of an RV or LV, such as the distal electrode 131 on the ventricular lead 107 as shown in FIG. 1. In various examples, the far-field EGM may be sensed between the ventricular electrode 131 and the proximal electrode 132, between the ventricular electrode 131 and the housing 116 or an electrode therein, or between the ventricular electrode 131 and a joint electrode comprising the proximal electrode 132 and the housing 116 or an electrode therein that are at least temporarily electrically tied together. Such far-field EGMs sensed using the ventricular electrode 131 may represents far-field LV or far-field BiV (i.e., LV and RV) activations, as well as ventricular synchrony as manifested by QRS width or interventricular conduction delay. Additionally or alternatively, the FFVA may be sensed using electrodes positioned in or on other heart chambers or locations other than RV and LV. In an example, the FFVA may be sensed using an atrial electrode, such as the RA electrode 111 associated with the lead 106, and a reference electrode such as the housing 116 or an electrode therein. In yet another example, the FFVA may be sensed using electrodes positioned in or on a His-bundle region, such as one of the electrodes 112A-112B associated with the lead 106, and a reference electrode such as the housing 116 or an electrode therein. In yet another example, the FFVA signal may include a subcutaneous ECG signal sensed using chest electrodes such as located at the housing 116. Such FFVA may contain information about ventricular synchrony, such as QRS width or interventricular conduction delay.

In some examples, the FFVA signal 222 may include a mechanical signal indicative of mechanical synchrony of contractions and vibrations between of the left and right ventricles. Examples of the mechanical signal may include an impedance signal, a heart sound signal, a pressure signal, among other hemodynamic signals that may be sensed using a physiologic sensor.

In some examples, portions of the His-bundle pacing system 200 may be implemented distributedly between two devices. In an example, a first device may include the electrostimulation circuit 210 and a stimulation delivery system such as the lead and associated electrodes for delivering the HBP pulses, and a second device may include the sensing circuit 220 and at least a portion of the control circuit 230. The sensing circuit 220 of the second device may be configured to sense, among other signals, the far-field ventricular response to the HBP pulses. In an example, the first and second devices are both implantable devices. In another example, at least one of the first or the second device is a non-implantable, wearable device.

The control circuit 230 may be configured to verify that the HBP pulses capture one or more conductive tissue such as the His bundle or the myocardium, and control the delivery of HBP pulses using the capture status. In an example, the control circuit 230 can be implemented as a part of a microprocessor circuit in the cardiac disease management system 100. The microprocessor circuit can be a dedicated processor such as a digital signal processor, application specific integrated circuit (ASIC), microprocessor, or other type of processor for processing information including heart sounds. Alternatively, the microprocessor circuit can be a general-purpose processor that can receive and execute instructions of performing the functions, methods, or techniques described herein.

As illustrated in FIG. 2, the control circuit 230 may include circuit sets comprising a capture verification circuit 232, a pacing threshold test circuit 233, and a stimulation control circuit 236. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The capture verification circuit 232 may include a cardiac synchrony detector 234 configured to determine a cardiac synchrony indicator using the sensed FFVA signal 222 in response to HBP pulses, and verify the His-bundle capture status using the cardiac synchrony indicator. The cardiac synchrony detector 234 may detect a QRS complex from the sensed far-field EGM, and measure the QRS width, and decides that a cardiac synchrony is restored if the measured QRS width falls below a threshold value or a percentage threshold (e.g., QRS narrowing by at least 20%). In an example, the QRS width threshold is approximately 80-120 milliseconds (msec). In some examples, the QRS width threshold may be independently determined for the far-field EGM sensor vectors.

In some examples, the cardiac synchrony detector 234 may determine a cardiac synchrony indicator using a QRS width trend over time. The cardiac synchrony detector 234 may detect a change in QRS width over time, such as a sudden decrease in QRS width from the previous QRS width or from a running-averaged QRS width. Such a sudden decrease in QRS width may indicate a restoration of cardiac synchrony produced by the HBP, corresponding to a transition from no His-bundle capture (e.g., para-Hisian capture, LOC, or HBP delivered at a site proximal to the blockage site) to His-bundle capture accompanied by HBP delivered at a site distal to the blockage site. In an example, a decrease of QRS width by 20% or more of the trended QRS width may indicate HBP capture and restoration of cardiac synchrony.

The capture verification circuit 232 may verify the His-bundle capture status using the determined cardiac synchrony indicator. If the cardiac synchrony indicator indicates restored synchrony (e.g., QRS width falling below a threshold), His-bundle capture is verified. Conversely, if the cardiac synchrony indicator indicates the pre-existing dyssynchrony remains (e.g., QRS width exceeding a threshold), no His-bundle capture is verified. Failure of restoration of cardiac synchrony may be resulted from para-Hisian myocardial capture, LOC, or a pacing site proximal of the blockage site on the His bundle.

Capture verification may be carried out according to a specified schedule, such as on a periodic basis, or continuously on a beat-by-beat basis (i.e., verifying capture in response to each HBP pulse). In an example, the cardiac synchrony detector 234 detects a QRS complex from the far-field EGM by comparing the EGM amplitude to a threshold. The QRS complex may be detected in a detection window that begins at the HBP pulse delivery and sustains for a specified duration. The duration may be determined by measuring QRS duration in the absence of pacing in patients having an underlying rhythm, or by measuring QRS duration during RV only pacing. The cardiac synchrony detector 234 determines the onset and termination of the QRS complex by comparing the QRS amplitude to the EGM baseline (e.g., an isoelectric line), and measures QRS width as a time duration from the onset to the termination of the detected QRS complex. The cardiac synchrony detector 234 then compares the QRS width to a threshold. If the measured QRS width falls below the threshold, the cardiac synchrony is restored; and the capture verification circuit 232 decides that His-bundle capture has occurred. If the measured QRS width exceeds the threshold, the cardiac dyssynchrony remains, and the capture verification circuit 232 decides that no His-bundle or bundle branch capture has occurred, or the pacing site is proximal to the blockage site such that no propagation of action potential would occur through the His-Purkinje system.

In some examples, His-bundle capture status may be determined additionally or alternatively using signal morphology of the FFVA 222. For example, the capture verification circuit 232 may determine a similarity metric between the far-field EGM morphology (e.g., QRS morphology) and a morphology template represented by morphological features of the same EGM vector corresponding to His-bundle capture and cardiac synchrony, and decides His-bundle capture if the similarity metrics satisfies a specified condition. In some examples, to improve reliability of His-bundle capture status decision, capture verification may be performed for a plurality of HBP pulses delivered over a number of cardiac cycles. A His-bundle capture is determined to have occurred if a substantial amount of the plurality of HBP pulses result in individual His-bundle captures.

In various examples, the capture verification circuit 232 may additionally determine the cardiac synchrony indicator using physiologic information indicative of cardiac mechanical activation, such as heart sounds, impedance, cardiac pressure, among other physiologic or hemodynamic parameters. Examples of detecting cardiac synchrony in response to HBP pulses, and thus determining the HBP capture status, are discussed below, such as with reference to FIG. 3.

The pacing threshold test circuit 233 may be configured to determine a HBP pacing threshold that represents minimal energy required to produce His-bundle capture. The pacing threshold may be determined during implantation of the IMD 104, and updated periodically at specified time period, or triggered by a specific event, such as when HBP pulses fail to capture the His bundle but instead consistently produce para-Hisian capture or LOC, or by a user command.

During a threshold test, the electrostimulation circuit 210 may deliver HBP pulses at or near the His bundle in accordance with a threshold test protocol. HBP pulses may be delivered at a rate 10-20 bpm above the measured atrial rate. The threshold test protocol may be machine-readable instructions stored in a memory device, and executable by a machine such as a microprocessor. The instructions specify programming a stimulation parameter to different values and measuring, for each programmed parameter value, a corresponding capture status. In various examples, the stimulation parameter, such as pulse amplitude, may be incremented following a ramp-up protocol, decremented following a ramp-down protocol, or sweep through a set of parameter values such as stored in a storage device. For each stimulation parameter value (e.g., pulse amplitude), the capture verification circuit 232 determines a capture status, such as using the QRS width measured from a far-filed ventricular activation signal. As the stimulation parameter value is changed such as according to the threshold test protocol, the pacing threshold test circuit 233 may detect a transition from a first capture status to a second capture status of a different type, and determine a HBP threshold using that detected transition of capture status. In an example, the pacing threshold test circuit 233 may generate a QRS width trend corresponding to multiple descending stimulation strength values in a ramp-down protocol. The pacing threshold test circuit 233 may detect from the QRS width trend a prolongation of QRS width exceeding a threshold, and determine the HBP threshold using the stimulation strength value corresponding to the detected prolongation of QRS width. In another example, the QRS width trend may correspond to multiple ascending stimulation strength values in a ramp-up protocol. The pacing threshold test circuit 233 may detect from the QRS width trend a shortening of QRS width falling below a threshold, and determine the HBP threshold using the stimulation strength value corresponding to the detected shortening of QRS width.

The stimulation control circuit 236 may be configured to adjust one or more therapy parameters using the verified His-bundle capture status, and to control the delivery of HBP pulses according to the adjusted therapy parameter. The stimulation control circuit 236 may include one or more of a pacing parameter adjuster circuit 237, a pacing site adjuster circuit 238, and a timing circuit 239. The pacing parameter adjuster circuit 237 may determine or update a stimulation parameter value using the HBP threshold provided by the pacing threshold test circuit 233, or the His-bundle capture status provided by the capture verification circuit 232. The stimulation parameter may be updated periodically at specified time period, triggered by a specific event, or by a user via a user interface 240. In an example, the pacing parameter adjuster circuit 237 may set the HBP pulse amplitude to the HBP threshold such as determined by the pacing threshold test circuit 233, plus a specified safety margin. The HBP threshold, after being generated, may change over time, such as due to changes in patient pathophysiology, medication, or lead migration or dislodgment. To maintain the desired capture status, the pacing parameter adjuster circuit 237 may dynamically adjust stimulation strength, and the pacing threshold test circuit 233 may accordingly update the HBP threshold. In addition to the stimulation strength, the pacing parameter adjuster circuit 237 may adjust one or more pulse width, pulse rate, pulse shape, among other pacing parameters, to more effectively activate the His-Purkinje system. In another example, the pacing parameter adjuster circuit 237 may adjust stimulation timing, such as an atrio-Hisian timing relative to an intrinsic or paced atrial event. In yet another example, the parameter adjuster circuit 237 may adjust stimulation mode, such as switching from AH mode to HV mode when a patient develops persistent or chronic atrial fibrillation, or treated with atrioventricular node ablation, or switch from AH pacing mode to AHV mode when the patient develops bundle branch block.

The pacing site adjuster circuit 238 may adjust stimulation site, such as by switching to a different stimulation vector configuration including a HBP electrode more distal than the existing electrode for delivering HBP pulses. As discussed above, effective propagation of the action potentials through the His-Purkinje system to restore cardiac synchrony can be achieved only if the HBP pulses are delivered distal to the blockage site. HBP pulses delivered proximal to the blockage site (i.e., above the blockage site), even if capable of activating the proximal portion of the His bundle, cannot cause the action potentials to propagate to the ventricles through the His-Purkinje system and produce synchronized ventricular contractions. If the capture verification circuit 232 decides that no His-bundle capture is indicated at a first His bundle site (e.g., para-Hisian myocardium capture, or LOC), or if the pacing threshold test circuit 233 determines a pacing threshold different from the existing pacing threshold, the pacing site adjuster circuit 238 may reconfigure the HBP pacing vector to deliver HBP pulses from a second His bundle site more distal than the first His bundle site, or to deliver HBP pulses from a bundle branch site (e.g., a left bundle branch site). In an example, the pacing site adjuster circuit 238 may adjust stimulation site if a specified number of attempts of pacing parameter adjustment (e.g., HBP pulse amplitude, pulse width, pulse rate, or pulse shape) still fail to restore ventricular synchrony.

The timing circuit 239 configured to time the delivery of the HBP pulses according to a stimulation timing parameter, such as an adjusted stimulation timing provided by the parameter adjuster circuit 237 or programmed by a user via a user interface 240. In an example, the timing circuit 239 may time the delivery of a HBP pulse using an atrio-Hisian (AH) window. The AH window is a programmable latency period with respect to an intrinsic (AS) or paced atrial event (AP). In an example, the AH window may be programmed to approximately 50 msec shorter than a sensed P wave-to-R wave (PR) interval or a programmed atrial-to-ventricular (AV) delay within a cardiac cycle. If an intrinsic His-bundle activity (Hs) is sensed within the AH window, the timing circuit 239 may initiate a His refractory period, during which a HBP pulse may be delivered. In another example, the AH window maybe determined using an intrinsic AH interval, such that the AH window may be programmed to slightly longer than the intrinsic AH interval (e.g., approximately 1-30 msec longer than the intrinsic AH interval). The HBP would then be timed off of a sensed atrial event but would occur just after the anticipated His event. The delivery of the HBP pulse may trigger a His capture verification window during which a far-field ventricular activation (e.g., QRS), or a cardiac mechanical signal, may be sensed.

The user interface 240 may include an input unit and an output unit. At least a portion of the user interface 240 may be implemented in the external system 140. The input unit may receive user input such as values of the parameters for physiologic event sensing, and His bundle response and myocardial response detections. The user input may receive user programming of stimulation parameters, or confirmation, rejection, or otherwise modification of the stimulation parameters generated by the parameter adjuster circuit 237, the pacing site generated by the pacing site adjuster circuit 238, or the timing of HBP generated by the timing circuit 239. The input unit may include an input device such as a keyboard, on-screen keyboard, mouse, trackball, touchpad, touch-screen, or other pointing or navigating devices.

The output unit may include circuitry configured to generate a human-perceptible notification of His-bundle capture status and/or various HBP thresholds. The output unit may be coupled to a display for displaying the received physiologic signals, including FFVA signals (e.g., EGMs, or cardiac mechanical activity signals), tracings of one or more of atrial EGM, His-bundle EGM, ventricular EGM, surface or subcutaneous ECG, or other sensor signals. The display may also display event sensing information such as intrinsic depolarizations, paced events (such as HBP pulses), and timing information on each of the sensed signals. The event sensing information may be overlaid with the signal tracings, or be displayed in a separate marker channel. The stimulation parameters, and intermediate measurements or computations may also be displayed. In an example, the output unit may generate a trend of the QRS width over time, such as a QRS width trend corresponding to multiple HBP pulses. The trend may be generated during HBP delivery, or during a HBP threshold test. The trend may be displayed to a user to help the user make programming changes to HBP therapy. The output unit may be coupled to a printer for printing hard copies of information about the event detection and therapy titration protocol. The information may be presented in a table, a chart, a diagram, or any other types of textual, tabular, or graphical presentation formats. The presentation of the output information may include audio or other media formats. In an example, the output unit may generate alerts, alarms, emergency calls, or other forms of warnings to signal the system user about the His-bundle capture status, cardiac synchrony restoration, present and recommended adjustment of HBP pacing site. In an example, the output unit may generate an alert when a loss of capture is indicated and a backup pacing is delivered. In another example, frequent backup pacing delivery may trigger the output unit to generate an alert and prompt a user (e.g., a clinician) to reprogram the pacing system.

Figure 3:
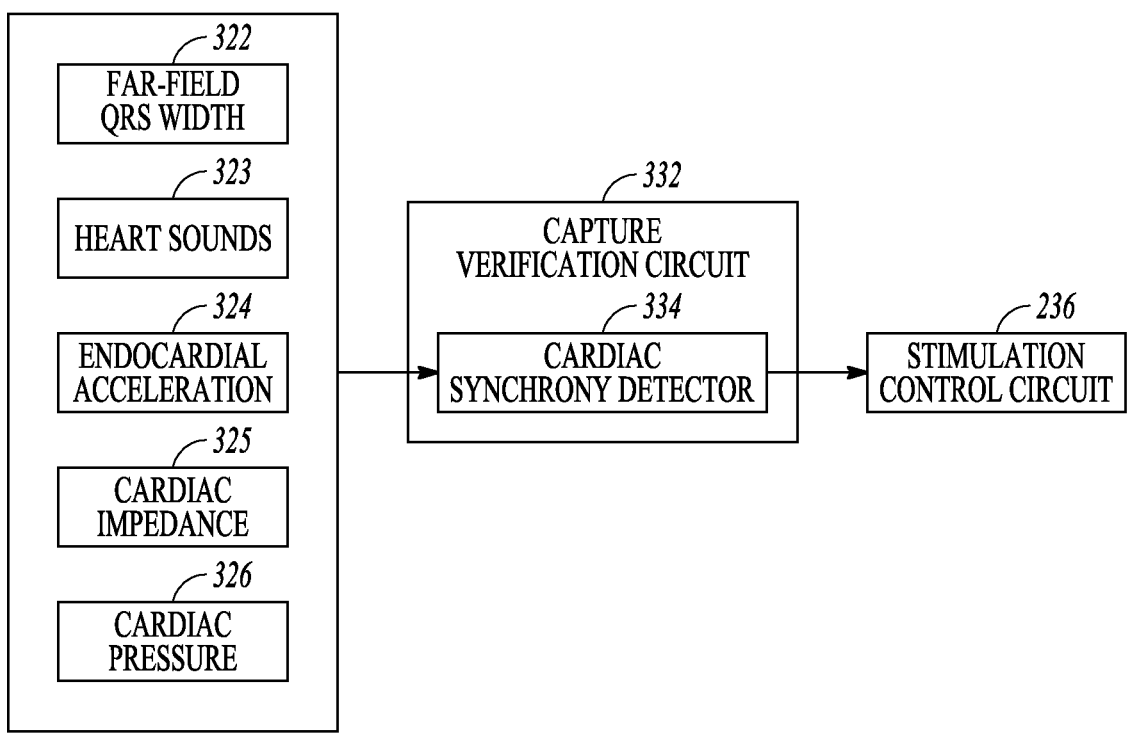
FIG. 3 is a block diagram illustrating generally an example of a portion of a HBP system that detects cardiac contractility and determine His-bundle capture status using one or more sensors.

FIG. 3 is a block diagram illustrating generally an example of a portion of a HBP system that detects cardiac contractility and determine His-bundle capture status using one or more sensors. The illustrated system portion, which can be a part of the His-bundle pacing system 200, includes a capture verification circuit 332 and a stimulation control circuit 236. The capture verification circuit 332 includes a cardiac synchrony detector 334 that may be configured to detect a change in cardia synchrony using one or more physiologic parameters 322-326. A far-field QRS width 322 may be detected measured using the far-field ventricular EGM. As discussed above with reference to FIG. 2, a narrow QRS resulted from the HBP delivery may be indicative of restoration of synchronized depolarization of the left and right ventricles, and thus HBP capture.

Heart sound (HS) information 323 in response to HBP delivery may be sensed using an accelerometer or a microphone sensor, positioned on a chest or in a heart chamber. Additionally or alternatively, an endocardial acceleration signal 324 may be sensed using lead-based electrodes positioned on a cardiac wall (e.g., endocardial or epicardial surface of a ventricle). HS metrics, such as intensity (e.g., amplitudes) of one or more of S1, S2, S3, or S4 heart sound components, timing parameters such as systolic timing intervals measured using the heart sound components, may be generated from the sensed HS information 323, or from the endocardial acceleration signal 324. One or more of the HS metrics may be used to evaluate changes in cardiac synchrony in response to HBP. For example, a decrease in S1 amplitude can be indicative of reduced contractility or contractile function. Systolic time intervals such as pre-ejection period (PEP), left-ventricular ejection time (LVET), a PEP-to-LVET ratio, can be indicative of contractile function (e.g., increase in PEP or PEP/LVET can be indicative of a decrease in contractility). S3 amplitude can be used to track fluid or preload changes, and is an early indicator of worsening heart failure (WHF). An increase in S3 (or S4) can be indicative of worsening of cardiac diastolic function. The capture verification circuit 332 may determine restoration of cardiac synchrony, and thus a His-bundle capture, if the S1 amplitude exceeds a threshold, or if a PEP or PEP/LVET falling below respective thresholds, or if the S3 or S4 amplitude falls below respective thresholds.

Cardiac impedance information 325 in response to HBP delivery may be sensed using impedance plethysmography methods via body surface electrodes or subcutaneously placed electrodes, such as electrodes placed in or on the heart. Impedance plethysmography may be used to estimate beat-by-beat cardiac output measurement, which provides an estimate of stroke volume from changes in the electrical impedance of the thorax during cardiac systole. The derivative or differential impedance signal (dZ/dt) represents a rate of cardiac volume change, and indicative of cardiac contractility. In an example, the capture verification circuit 232 may measure a Q-E period from the Q wave in an ECG to the maximal value of the dZ/dt signal. A shorter Q-E period may correspond an increase in cardiac contractility. Alternatively, the capture verification circuit 232 may determine a Heather index represented by a ratio of the maxima amplitude of dZ/dt signal to the Q-E period. An increase in the Heather index corresponds to an increase in cardiac contractility. The capture verification circuit 332 may determine restoration of cardiac synchrony, and thus a His-bundle capture, if an increase in impedance-based contractility measurement, such as an increase in one or more of dZ/dt, Q-E period, or the Heather index, exceeds their respective thresholds.

Cardiac pressure information 326 in response to HBP delivery may be sensed using an indwelling pressure sensor within a catheter or lead, or a leadless implantable pressure sensor. In an example, the capture verification circuit 232 may measure a rate of change of cardiac pressure (dP/dt) which is indicative of cardiac contractility. An increase in pressure-based contractility measurement, such as an increase in dP/dt, can be indicative of restoration of cardiac synchrony. The capture verification circuit 332 may determine restoration of cardiac synchrony, and thus a His-bundle capture, if the dP/dt increases and exceeds a threshold.

In various examples, the cardiac synchrony detector 334 may determine a cardiac synchrony indicator using a combination of two or more of the physiologic parameters 322-326. Example of the combination may include weighted combination, or other linear or nonlinear combinations, of the changes of two or more physiologic parameters in response to the HBP delivery. The capture verification circuit 332 may determine a His-bundle capture if the combination of the physiologic parameter changes indicate a restoration of cardiac synchrony.

Figure 4A:
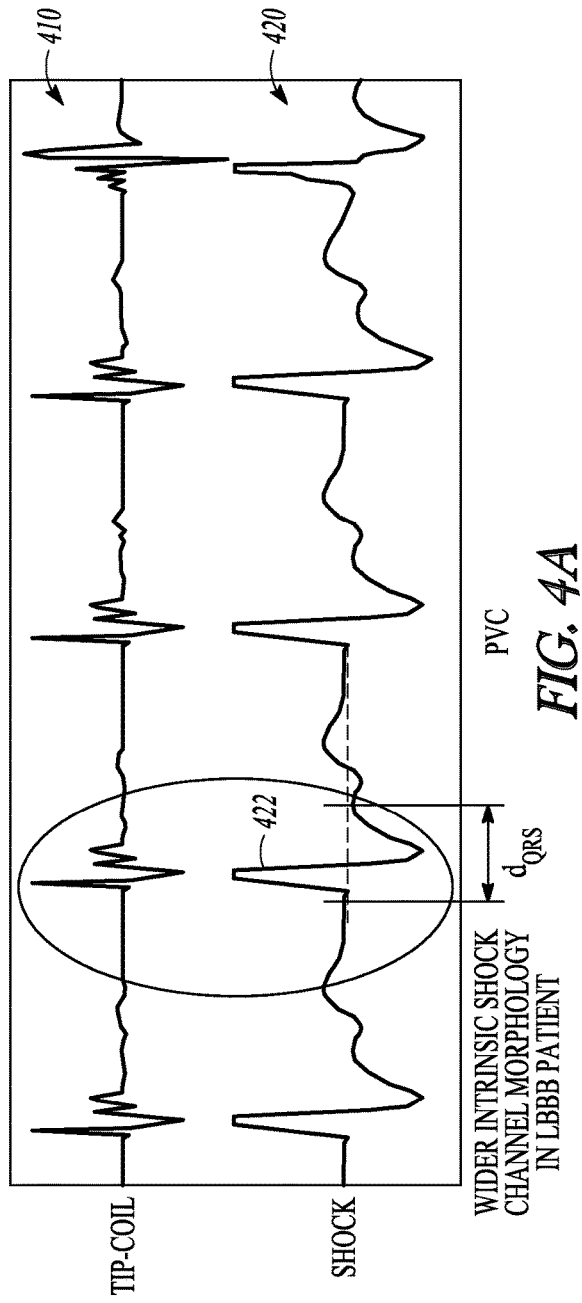
FIGS. 4A-4B are diagrams illustrating an example of restoration of ventricular synchrony by distal HBP as detected from far-field ventricular activation.
Figure 4B:
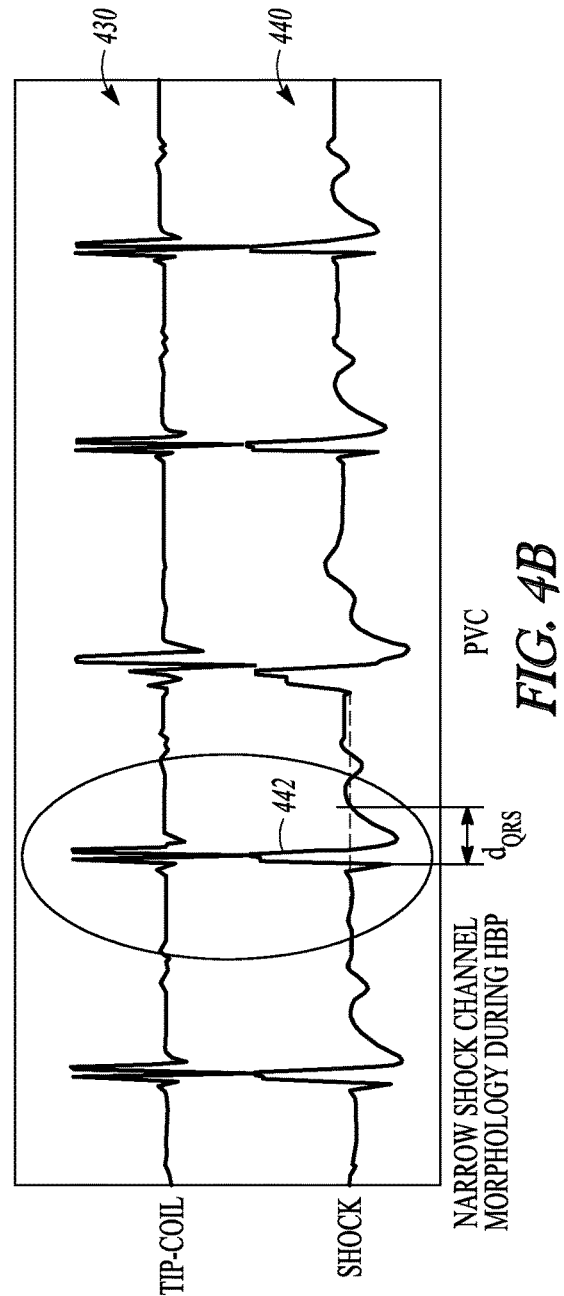

FIGS. 4A-4B are diagrams illustrating an example of restoration of ventricular synchrony by distal HBP as detected from FFVA. In the illustrated example, intracardiac near-field ventricular EGM (410 and 430) and far-field ventricular EGM (420 and 440) were concurrently recorded from a heart failure patient, such as using the sensing circuit 220 of the HBP system 200. The near-field ventricular EGM may be sensed between an RV tip electrode and an RV coil electrode. The far-field ventricular EGM may be sensed between the RV coil and a SVC coil, such as the electrodes 131 and 132 respectively shown in FIG. 1. The far-field ventricular EGM may be filtered using a bandpass filter with a wide passband, such as approximately 3-50 Hz. Such a wide band filter may help improve the accuracy of QRS width measurement. FIG. 4A illustrates a near-field ventricular EGM portion 410 and a far-field ventricular EGM portion 420 during an intrinsic heart rhythm (i.e., no HBP being delivered). The heart failure patient has a LBBB, as manifested by wide QRS complex 422 on the far-field EGM 420. The cardiac synchrony detector 234 may measure a pre-HBP QRS width, $d_{QRS}(1)$, from the far-field EGM 420. FIG. 4B illustrates a near-field ventricular EGM portion 430 and a far-field ventricular EGM portion 440 during distal His-bundle pacing. The cardiac synchrony detector 234 may detect a QRS complex 442 from the far-field EGM 440, and measure the QRS width, $d_{QRS}(2)$, in response to the HBP delivery. In the illustrated example, $d_{QRS}(2)$ is shorter than the pre-HBP $d_{QRS}(1)$. The capture verification circuit 232 may compare the $d_{QRS}(2)$ to a threshold or a percentage threshold (e.g., approximately 20% reduction from $d_{QRS}(1)$), and determines that the distal HBP pulses have successfully produced His-bundle capture and synchronized ventricular contractions if the $d_{QRS}(2)$ falls below the threshold (e.g., $d_{QRS}(2)$ is 20% or more shorter than $d_{QRS}(1)$).

Figure 5:
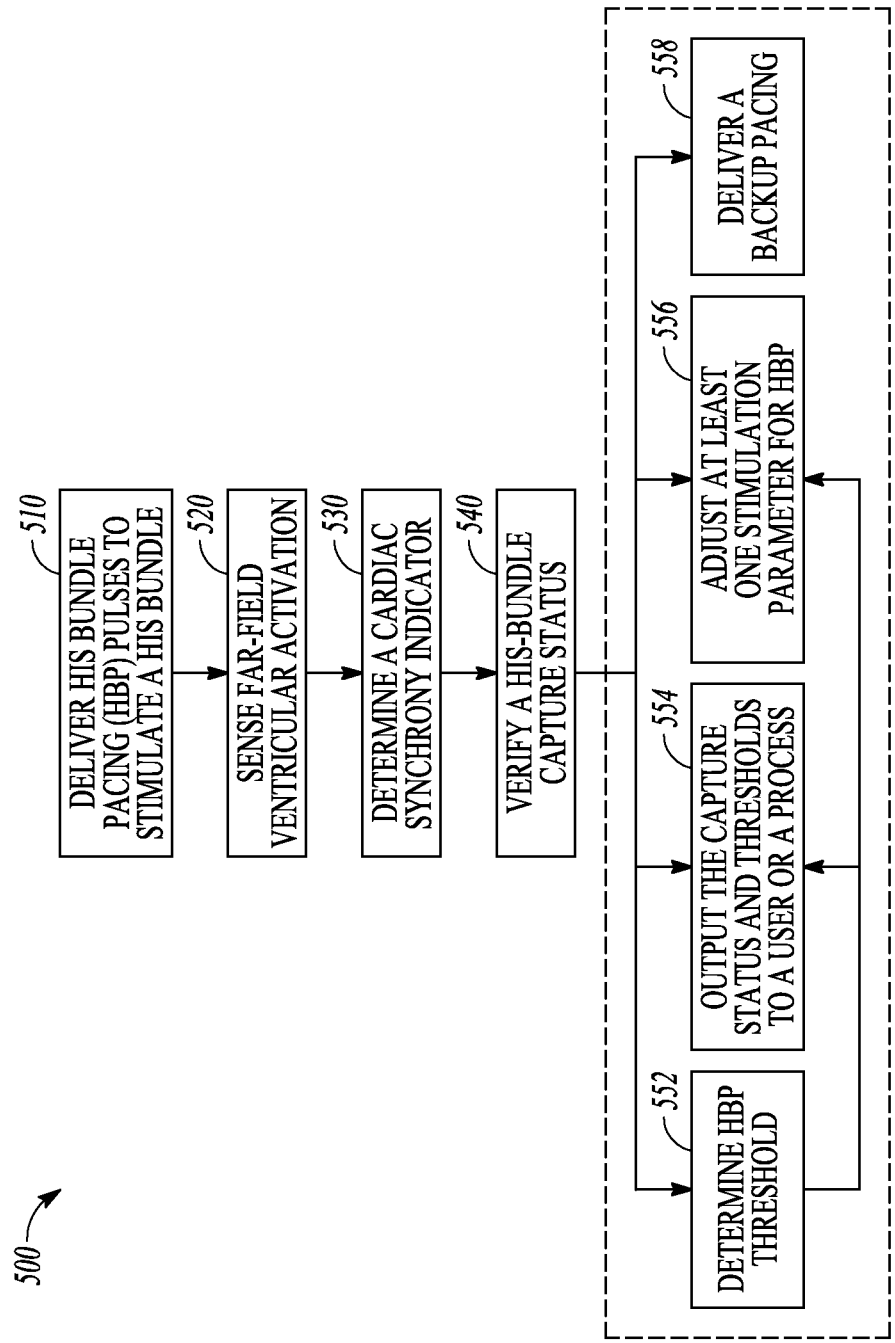
FIG. 5 is a flowchart illustrating generally an example of a method 500 for providing HBP to a patient using a medical system.

FIG. 5 is a flowchart illustrating generally an example of a method 500 for providing His-bundle pacing (HBP) to a patient using a medical system. The method 500 may be implemented and executed in an ambulatory medical device such as an implantable or wearable medical device, or in a remote patient management system. In an example, the method 500 may be implemented in, and executed by, the IMD 104, one or more devices in the external system 140, or the His-bundle pacing system 200.

The method 500 commences at 510, where pacing pulses may be generated and delivered to a target site to stimulate the His bundle of the patient heart. The target site may include a region at or near the His bundle 121, such as a region distal to the blocked or slowly conducting AV node and in the AV septum, an interventricular septum region, or a bundle branch such as a left bundle branch. The pacing pulses may be generated by the electrostimulation circuit 210, according to programmed stimulation parameters. Examples of the stimulation parameters may include stimulation site, stimulation mode, stimulation timing, or stimulation strength, among other parameters. The stimulation strength parameters determine the amount of energy delivered to the pacing site, and may include pulse amplitude, pulse width, pulse frequency, pulse waveform, duty cycle, or stimulation duration. In an example, the pacing pulses may be programmed with different stimulation strength values, such as pulse amplitudes. The pacing pulses may be delivered via a delivery system including, for example, the lead 106 and one or more of the electrodes 112A-112B. In an example, the pacing pulses may be delivered in multiple cardiac cycles, such that at least one pulse is delivered within each of the multiple cardiac cycles.

At 520, a far-field ventricular activation (FFVA) signal may be sensed in response to the delivery of the pacing pulses, such as using the sensing circuit 220. The FFVA signal may include a far-field electrical signal (e.g., an electrogram) indicative of electrical synchrony of depolarizations of the left and right ventricles in response to the HBP delivery. The far-field EGM may be sensed using a unipolar or a bipolar configuration. In an example, the far-field EGM may be sensed using the distal electrode 131 and the proximal electrode 132, or using the ventricular electrode 131 and the housing 116 or an electrode therein, or using the ventricular electrode 131 and a joint electrode comprising the proximal electrode 132 and the housing 116 or an electrode therein that are at least temporarily electrically tied together. The far-field EGM may alternatively be sensed using the RA electrode 111 and a reference electrode such as the housing 116 or an electrode therein, or using one of the His-bundle electrodes 112A-112B and a reference electrode such as the housing 116 or an electrode therein. The FFVA signal may alternatively include a surface ECG or a subcutaneous ECG signal. In some examples, the FFVA signal may include a mechanical signal indicative of mechanical synchrony of contractions and vibrations between of the left and right ventricles.

At 530, a cardiac synchrony indicator may be determined using the sensed FFVA in response to HBP pulses. In an example, a QRS complex may be detected from the sensed far-field EGM, and a QRS width measured, using the cardiac synchrony detector 234. Restoration of cardiac synchrony is determined if the measured QRS width falls below a threshold. The QRS width threshold may be independently determined for the far-field EGM sensor vectors. In another example, QRS width may be measured over multiple cardiac cycles and trended over time. Restoration of cardiac synchrony produced by the HBP is determined if a change in QRS width, such as a sudden decrease in QRS width from the previous QRS width or from a running-averaged QRS width, exceeds a threshold. In various examples, the cardiac synchrony indicator may be determined further using physiologic information indicative of cardiac mechanical activation, such as one or more of heart sounds, impedance, cardiac pressure, among other physiologic or hemodynamic parameters, such as described above with reference to FIG. 3.

At 540, His-bundle capture status may be verified using the cardiac synchrony indicator. If the cardiac synchrony indicator indicates restored synchrony (e.g., QRS width falling below a threshold), then His-bundle capture is verified. Otherwise, if the pre-existing dyssynchrony remains (e.g., QRS width exceeding a threshold), then no His-bundle capture is verified. In some examples, the His-bundle capture status may be determined additionally or alternatively using signal morphology of the FFVA. For example, if the far-field EGM morphology (e.g., morphology of QRS) is morphologically similar to a morphology template represented by morphological features of the same EGM vector corresponding to His-bundle capture and cardiac synchrony (e.g., a similarity score, of a distance in a morphological feature space, between the far-field EGM morphology and the template falls within a specified range), then a His-bundle capture is determined to have occurred. Failure of restoration of cardiac synchrony may be resulted from para-Hisian myocardial capture, LOC, or HBP delivered at a side proximal to the blockage site.

The His-bundle capture status as verified at 540 may be output to one or more diagnostic or therapeutic processes. In one example, a HBP threshold may be determined at 552, such as by using the pacing threshold test circuit 233. The HBP threshold may be determined during implantation of the IMD 104, and updated periodically at specified time period, or triggered by a specific event, such as when HBP pulses fail to capture the His bundle but instead consistently produce para-Hisian capture or LOC, or by a user command. During the threshold test, stimulation parameter, such as pulse amplitude, may be incremented following a ramp-up protocol, decremented following a ramp-down protocol, or sweep through a set of stored parameter values. Capture status may be verified at each pacing parameter value, such as using QRS width. A HBP threshold may be determined at 552 using a prolongation of QRS width exceeding a threshold during a ramp-down protocol with decreasing stimulation amplitudes, or using a shortening of QRS width falling below a threshold in a ramp-up protocol with increasing stimulation amplitudes.

At 554, the His-bundle capture status, and optionally the HBP threshold, may be output to a user (e.g., a clinician) or a process at 552, such as being displayed on a display of the user interface 240. The QRS width trend, along with the sensed physiologic signals, such as those illustrated in FIG. 3, or the programmed stimulation parameters, among other intermediate measurements or computations, may also be displayed.

Additionally or alternatively, at 556, one or more stimulation parameters may be adjusted using the capture status at 540 and optionally the HBP threshold determined at 552, such as via the parameter adjuster circuit 237. The adjustment may include switching to a different HBP pacing site, or using pacing vector configuration. For example, if no His-bundle capture is indicated at a first His bundle site (e.g., para-Hisian myocardium capture, or LOC), then the HBP pacing vector may be reconfigured to deliver HBP pulses from a second His bundle site more distal than the first His bundle site, or to deliver HBP pulses from a left bundle branch site. In another example, the adjustment may include adjusting timing of HBP pulses with respect to an intrinsic or paced atrial activation, adjusting stimulation strength such as one or more of pulse amplitude, pulse width, pulse frequency, pulse waveform, duty cycle, or stimulation duration. In some examples, stimulation parameter adjustment may be using capture statistics computed using the capture verification results over multiple heart beats. Examples of the capture statistics may include percentages, histograms, or other measures of distribution of the selective His-bundle capture, non-selective His-bundle capture, or para-Hisian capture. In some examples, the HBP pulse amplitude to the HBP threshold such as determined by the pacing threshold test circuit 233, plus a specified safety margin.

At 558, a backup pacing may be delivered when certain capture status results, such as a LOC, or a para-Hisian capture. The backup pacing may be delivered to a target ventricular site via a lead with associated electrodes disposed in or on a ventricle, such as a right ventricle. Additionally or alternatively, the backup pacing may be delivered at or near the His bundle. In an example, the backup pacing pulses include high-output pacing (HOP) pulses with higher pacing energy than conventional pacing pulses. In some examples, the HOP pulses may be delivered on an intermittent basis, such that the conventional pacing pulses are delivered in 3-5 cardiac cycles between the HOP pulses. In addition to backup ventricular pacing, other therapies, such as CRT, BiV pacing, LV-only pacing, single site LV pacing, or multi-site LV pacing may be delivered to improve myocardial contractility and cardiac performance.

Various embodiments are illustrated in the figures above. One or more features from one or more of these embodiments may be combined to form other embodiments.

The method examples described herein can be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code can form portions of computer program products. Further, the code can be tangibly stored on one or more volatile or non-volatile computer-readable media during execution or at other times.

The above detailed description is intended to be illustrative, and not restrictive. The scope of the disclosure should therefore be determined with references to the appended claims, along with the full scope of equivalents to which such claims are entitled.

What is claimed is:

1. A system for pacing a heart, comprising:
   an electrostimulation circuit configured to generate electrostimulation pulses to stimulate a His bundle or a bundle branch of the heart;
   a sensing circuit configured to sense a far-field ventricular activation using at least a chest electrode; and
   a control circuit, including a capture verification circuit configured to:
      determine a cardiac synchrony indicator using the sensed far-field ventricular activation in response to the electrostimulation of the His bundle or the bundle branch; and
      verify a capture status using the determined cardiac synchrony indicator.

2. The system of claim 1, wherein:
   the sensing circuit is configured to sense the far-field ventricular activation including a far-field electrogram in response to the stimulation of the His bundle or the bundle branch, and to measure a QRS width using the sensed far-field electrogram; and
   the capture verification circuit is configured to verify the capture status using the measured QRS width.

3. The system of claim 2, wherein the capture verification circuit is configured to verify the capture status as one of:
   a His-bundle capture if the measured QRS width falls below a threshold; or
   a para-Hisian capture or a loss of capture if the measured QRS width exceeds the threshold.

4. The system of claim 1, wherein:
   the sensing circuit is configured to sense the far-field ventricular activation including a far-field electrogram in response to the stimulation of the His bundle or the bundle branch; and
   the capture verification circuit is configured to verify the capture status using a comparison of the sensed far-field electrogram to a morphology template.

5. The system of claim 1, wherein the capture verification circuit configured to, in response to the stimulation of the His bundle or the bundle branch, determine the cardiac synchrony indicator further using one or more of:
   heart sounds information;
   endocardial acceleration information;
   cardiac impedance information; or
   cardiac pressure information.

6. The system of claim 1, wherein the control circuit is configured to adjust a therapy parameter using the verified capture status, and to control the stimulation of the His bundle or the bundle branch according to the adjusted therapy parameter.

7. The system of claim 6, wherein the therapy parameter includes one or more of:
   a pacing site for delivering stimulation pulses;
   a pulse amplitude;
   a pulse width; or
   a pulse rate.

8. The system of claim 6, wherein the control circuit is configured to, in response to a para-Hisian capture or a loss of capture produced by stimulation at a first His bundle site, control the electrostimulation circuit to stimulate a second His bundle site more distal than the first His bundle site or a left bundle-branch site.

9. The system of claim 1, wherein the control circuit includes a pacing threshold test circuit coupled to the capture verification circuit, wherein:
   the capture verification circuit is configured to verify capture status in response to electrostimulation pulses having multiple stimulation strength values according to a threshold test protocol; and
   the pacing threshold test circuit is configured to determine, using the verified capture status, a pacing threshold.

10. A system for pacing a heart, comprising:
    an electrostimulation circuit configured to generate electrostimulation pulses to stimulate a His bundle or a bundle branch of the heart;
    a sensing circuit configured to sense a far-field ventricular activation; and
    a control circuit, including a capture verification circuit configured to:
       determine a cardiac synchrony indicator, in response to the stimulation of the His bundle or the bundle branch, using (i) the sensed far-field ventricular activation and (ii) at least one of one or more of heart sounds information, endocardial acceleration information, cardiac impedance information, or cardiac pressure information; and
       verify a capture status using the determined cardiac synchrony indicator.

11. The system of claim 10, wherein the sensing circuit is configured to sense the far-field ventricular activation including a far-field electrogram in response to the stimulation of the His bundle or the bundle branch, and to measure a QRS width using the sensed far-field electrogram; and
    the capture verification circuit is configured to verify the capture status using the measured QRS width.

12. The system of claim 11, wherein the capture verification circuit is configured to trend the QRS width over time, and to verify the capture status in response to a change in QRS width over time satisfying a condition.

13. The system of claim 10, wherein the control circuit is configured to adjust a therapy parameter using the verified capture status, and to control the stimulation of the His bundle or the bundle branch according to the adjusted therapy parameter.

14. The system of claim 13, wherein the control circuit is configured to increase at least one a pulse amplitude, pulse width, or pulse rate of the electrostimulation pulses in response to a para-Hisian capture or a loss of capture.

15. The system of claim 13, wherein the sensing circuit is configured to sense the far-field ventricular activation using at least one of:
- a chest electrode;
- a ventricular electrode;
- an atrial electrode; or
- a His-bundle electrode.

16. A system for pacing a heart, comprising:
an electrostimulation circuit configured to generate electrostimulation pulses to stimulate a His bundle or a bundle branch of the heart;
a sensing circuit configured to sense a far-field ventricular activation; and
a control circuit, including:
a capture verification circuit configured to, in response to electrostimulation of the His bundle or the bundle branch according to a threshold test protocol comprising multiple stimulation strength values, (i) determine a cardiac synchrony indicator using the sensed far-field ventricular activation and (ii) verify a capture status using the determined cardiac synchrony indicator; and
a pacing threshold test circuit configured to determine a pacing threshold using the verified capture status.

17. The system of claim 16, wherein the threshold test protocol includes a stimulation strength ramp-down protocol, and the pacing threshold test circuit is configured to determine the pacing threshold corresponding to a prolongation of QRS width exceeding a threshold.

18. The system of claim 16, wherein the threshold test protocol includes a stimulation strength ramp-up protocol, and the pacing threshold test circuit is configured to determine the pacing threshold corresponding to a shortening of QRS width falling below a threshold.

19. The system of claim 16, wherein:
the sensing circuit is configured to sense the far-field ventricular activation including a far-field electrogram in response to the stimulation of the His bundle or the bundle branch; and
the capture verification circuit is configured to verify the capture status using a comparison of the sensed far-field electrogram to a morphology template.

20. The system of claim 16, wherein the control circuit is configured to adjust a therapy parameter using the verified capture status, and to control the stimulation of the His bundle or the bundle branch according to the adjusted therapy parameter.

* * * * *